United States Patent [19]

Kline

[11] 4,044,765
[45] Aug. 30, 1977

[54] FLEXIBLE TUBE FOR INTRA-VENOUS FEEDING

[75] Inventor: William Mathes Kline, Gloversville, N.Y.

[73] Assignee: Medical Evaluation Devices and Instruments Corporation, Gloversville, N.Y.

[21] Appl. No.: 641,690

[22] Filed: Dec. 17, 1975

[51] Int. Cl.² ........................ A61M 5/00; A61M 25/00
[52] U.S. Cl. ................................. 128/214.4; 128/348; 128/DIG. 16
[58] Field of Search ............ 128/2 M, DIG. 9, 214.4, 128/348-351, DIG. 16

[56] References Cited

U.S. PATENT DOCUMENTS

| | | | |
|---|---|---|---|
| 3,406,685 | 10/1968 | May | 128/214.4 |
| 3,467,101 | 9/1969 | Fogarty et al. | 128/348 |
| 3,500,828 | 3/1970 | Podhora | 128/214.4 |
| 3,618,613 | 11/1971 | Schulte | 128/348 |
| 3,757,768 | 9/1973 | Kline | 128/348 X |

FOREIGN PATENT DOCUMENTS

| | | | |
|---|---|---|---|
| 2,088,868 | 7/1972 | France | 128/349 R |
| 1,007,476 | 5/1957 | Germany | 128/348 |
| 4,816 | 3/1889 | United Kingdom | 128/349 R |
| 785,136 | 10/1957 | United Kingdom | 128/349 R |

Primary Examiner—Dalton L. Truluck
Attorney, Agent, or Firm—Thomas E. Tate

[57] ABSTRACT

The disclosure is that of an invention directed to a flexible tube for intra-venous feeding, the proximal end of which is permanently and leak-proofedly affixed to a connecting hub and the distal end of which comprises a hollow tip configured to closely but freely retain the distal portion of a removable puncture needle. A puncture needle is provided to effect initial insertion into a vein of an animate being; and a sight zone is provided in either or both of the flexible tube and the handle of the puncture needle for visual observation of liquid flow. There is also disclosed a method of internally coating the inner body of the tube and for externally sheathing the inner body by extrusion coating.

5 Claims, 8 Drawing Figures

FLEXIBLE TUBE FOR INTRA-VENOUS FEEDING

THE INVENTION

This invention relates generally to new and useful improvements in devices used for intra-venous feeding of animate beings and particularly seeks to provide a novel flexible tube for such purposes.

It is believed that, originally, I.V. tubes were made of a frangible material such as glass, with consequent risks to the patient due to breaking of the tube during or after insertion thereof into a vein or to movements of the patient that would cause discomfort, breaking of the tube or even perforation of the vein wall; or, more recently, were made of vinyl or other relatively rigid plastic material that eliminated only the breakage problem while introducing the new problem of flow reduction or stoppage due to wall collapse or kinking resulting from a patient's movements.

Still more recently, a flexible I.V. tube, such as that disclosed in U.S. Pat. No. 3,757,768, has been developed to overcome the above mentioned problems of breaking, kinking or wall collapsing.

More specifically, the I.V. tube of the present invention is a marked improvement over that disclosed in the above mentioned patent in that it may provide an inert interior coating as well as the inert exterior sheath or coating; it provides a sight zone for visual observation of blood flow to determine accuracy of initial insertion into a vein and for subsequent visual observation of the flow of I.V. fluid; its distal tip not only restrains the body spring from axial elongation but also is progressively drawn down or tapered for easier insertion into the vein and for closely but freely engaging around a removable puncture needle; and it provides a reinforced leak-proof connection with the hub fitting at its proximal end.

Therefore, an object of this invention is to provide a novel intra-venous tube assembly that includes a flexible I.V. tube and a relatively rigid removable, internally disposed, puncture needle for effecting the initial introduction of the distal end of the I.V. tube into a vein of an animate being.

Another object of this invention is to provide a device of the character that includes a sight zone for visible observation of any liquid flowing therethrough.

Another object of this invention is to provide an I.V. tube of the character stated that includes a hollow axially extending distal tip that is drawn down or tapered to fit closely but freely around the distal end portion of the puncture needle.

Another object of this invention is to provide an I.V. tube of the character stated that includes a body formed from a continuously wound coil spring in which the helices thereof are in mutual contact and in which the spring is at least externally sheathed with a smooth inert impervious transparent plastic material firmly bonded thereto and which may also include an internal coating formed from the same type of plastic material as that of the external sheathing.

Another object of this invention is to provide an I.V. tube of the character stated in which the tapered distal tip is formed as an extension of the external sheathing and in which any internal coating is coextensive in length with the distal tip and bonded thereto in such a manner as to form a single wall, the proximal end of which encloses the distal coil of the body spring.

A further object of this invention is to provide an I.V. tube of the character stated that includes a hub at its proximal end and fitted thereto in a reinforced and leak-proof manner for the initial reception and frictional retention of the proximal manipulating handle of the puncture needle and for subsequent connection to a source of I.V. fluid after the puncture needle has been withdrawn.

A further object of this invention is to provide a novel method for internally coating the spring of the I.V. tube together with the distally extending hollow tip thereof.

A further object of this invention is to provide a novel method of applying the external sheathing to the body springs either by extrusion coating a continuously presented series of successively spaced spring bodies or a continuously presented series of successively spaced spring bodies that are interconnected by removable configuration-determining pins.

A further object of this invention is to provide an I.V. tube assembly of the character stated that is simple in design, rugged in construction and economical to manufacture.

With these and other objects, the nature of which will become apparent, the invention will be more fully understood by reference to the drawings, the accompanying detailed description and the appended claims.

Figure 1:
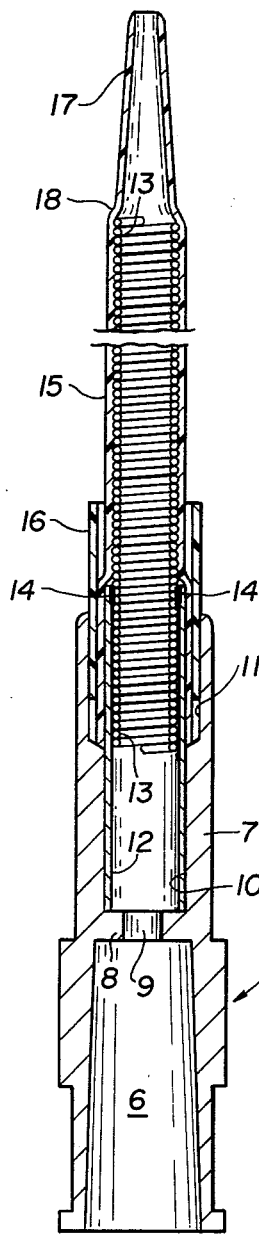
FIG. 1 is an enlarged longitudinal section of a flexible I.V. tube constructed in accordance with this invention.

Referring to the drawings in detail the invention, as illustrated, is embodied in an intra-venous feeding tube assembly (see FIG. 1) that includes a hub generally indicated 5, preferably formed from metal, and having a proximal generally cylindrical end cavity or socket 6 for the initial frictional retention of the handle of a puncture needle, as will be hereinafter more fully described, and for subsequent connection to a source of I.V. fluid.

The distal end of the hub 5 is formed as a bell housing 7 for the reception and permanent leak proof retention of the proximal end of a flexible I.V. tube and includes a transverse web 8 having a central aperture 9 through which the puncture needle initially passes and through which the I.V. fluid passes after the puncture needle has been removed. The bell housing 7, distally of the web 8, is provided with two serially arranged cylindrical cavities 10, 11 of which the distal cavity 11 has a diameter somewhat greater than that of the cavity 10.

A metal sleeve or cannula 12, having a length somewhat greater than the combined lengths of the cavities 10 and 11 and an outside diameter complementary to the cavity 10, has its proimal end fitted into the cavity 10 and secured therein by swaging or other suitable means. The distal end portion of the sleeve 12 extends through and beyond the cavity 11, thus defining an annular void between the outer wall of the sleeve and the inner wall of that cavity.

A close wound helical spring 13, having an outside diameter complementary to the inside diameter of the sleeve 12 and a length corresponding to the desired length of the I.V. tube, has its proximal end fitted within the distal end portion of the sleeve 12 to the depth of the cavity 11 and is secured therein as by an annular weld 14 or other suitable means.

A tubular outer sheath 15, formed from a suitable inert, heat-shrinkable, flexible, transparent plastic material such as halogenated hydrocarbon, polyethylene, polypropylene or polyurethane, and having a length somewhat greater than the finished length of the flexible I.V. tube, is freely fitted over the spring 13 with its proximal end retained within the void between the distal portion of the sleeve 12 and the wall of the cavity 11. Because the distal lip of the bell housing 7 inadvertantly may become a shoulder against which the I.V. tube may kink due to rough or improper handling, a reinforcing sleeve 16, preferably formed from the same material as that of the sheath 15, is fitted over the proximal end portion of the sheath and has its proximal end portion disposed within the void surrounding the sleeve 12 and its distal end portion extending distally beyond the distal lip of the bell housing 7. At this stage both the outer sheath 15 and the reinforcing sleeve 16 are heat shrunk so that the sheath becomes fully bonded to the exposed portion of the spring 13 and with the associated portion of the sleeve 12 and the reinforcing sleeve 16 becomes fully bonded to its associated portion of the outer sheath.

Figure 3:
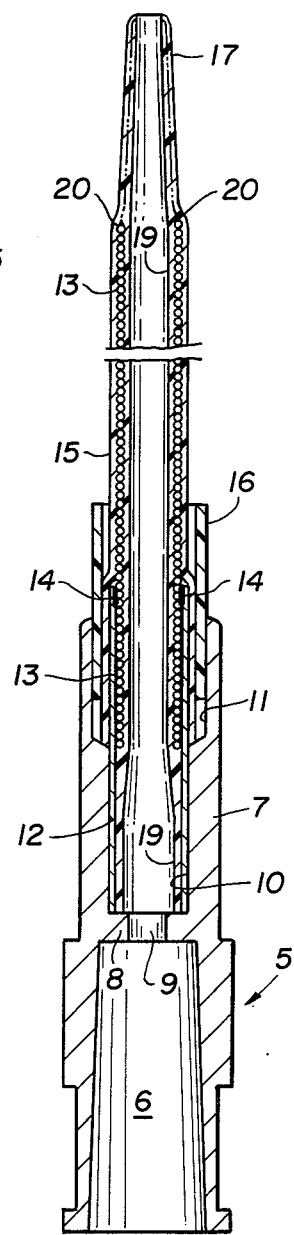
FIG. 3 is a view similar to FIG. 1 but additionally showing an inner coating of the body spring and of the distally extending hollow tip.

It should be noted at this point in the description that in the interest of clarity of illustration, FIGS. 1 and 3 show the reinforcing sleeve 16 as it would appear prior to heat shrinking and the outer sheath 15 as it appears after heat shrinking.

After the above mentioned heat shrinking has been completed, the wall of the cavity 11 is rolled or crimped into locking or securing contact with the associated portions of the reinforcing sleeve 16 and the sheath 15, thus completing the leakproof attachment of the proximal end of the spring 13 to the bell housing of the hub. It should be noted that FIGS. 1 and 3 show the condition of the hub before the above mentioned rolling or crimping has taken place.

The distally extending portion of the outer sheath 15 defines a hollow distal tip 17 that is necked down as at 18 to lock the distal end coils of the spring 13 against axial elongation. In order to provide a smooth entry of the I.V. tube into a vein, the distal tip 17 is either heat drawn or ground and polished into a taper such that its outer wall does not include any abrupt changes in diameter that otherwise would impede its smooth insertion into the vein and the distal tip portion of the lumen will closely, but freely, permit passage of the distal end of a puncture needle therethrough. After this taper of the hollow tip 17 has been established, the excess length of the tip is cut off to the length required for proper exposure of the point of the puncture needle and the raw edge at the cut-off is smoothed either by the application of heat or by further grinding and polishing.

As previously stated, one object of this invention is to provide a sight zone for visible observation of blood flow upon initial insertion of the puncture needle to determine whether or not the insertion has been accurately and properly effected.

Figure 2:
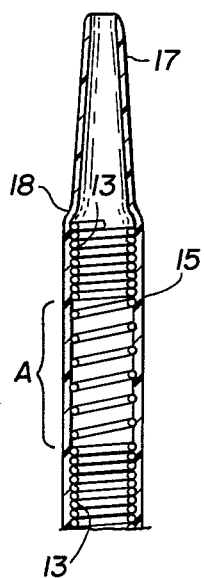
FIG. 2 is a detail view similar to the upper end of FIG. 1 but showing an intermediate sight zone that is effected by separating a plurality of the helices of the body spring.

One way of providing such a sight zone, as shown in FIG. 2, is to separate a plurality of the coils of the spring 13 in a zone indicated at A before the outer sheath 15 is applied to and heat shrunk thereon, thus providing gaps between the separated coils through which blood flow may be observed through the transparent outer sheath.

Another way of providing such a sight zone is to construct the puncture needle with a hollow transparent handle or manipulating knob as will be hereinafter more fully described in connection with the puncture needle.

Regardless of whether or not a sight zone is provided intermediate the ends of the flexible I.V. tube, it may be desirable to internally line or coat the tube as shown in FIG. 3 of the drawings.

For this purpose, a solution, emulsion or dispersion of the same type of inert plastic as that used for the outer sheath 15 is forced into the lumen of the tube and then allowed to drain, after which a blunt end stylette, having a diameter of about 0.002 less than that of the lumen of the spring 13, is inserted to clear any obstruction and to smooth any roughness, thus leaving a deposited inner coating or lining 19 which is dried or cured by heating the entire unit to about 250° F for about 10 minutes. The clearing stylette may be either removed from or retained within the unit during heat curing of the inner coating.

If a single application as described above does not produce an inner coating of the desired thickness, successive additional application may be made in the same manner until the desired thickness has been attained.

This inner coating 19 also lines the distally extending hollow tip 17, which is then subjected to heat sufficient to approach the melt point of the plastic, so that the outer sheath and the inner coating will coalesce and form a single continuous wall, the proximal end of which covers the distal coil of the spring 13, as at 20, to prevent axial elongation of the spring.

It will have been understood from the foregoing portions of this description that a puncture needle must be used in connection with the I.V. tube in order for the tube to be easily and properly inserted into a vein. Further, the puncture needle also can be constructed to provide either a sole sight zone or one that supplements the sight zone A of the I.V. tube in the modification of FIG. 2 and also can function as an aspirating needle when connected to the barrel of a hypodermic syringe, thus enabling a blood sample to be taken as an incident precedent to I.V. feeding.

Figure 4:
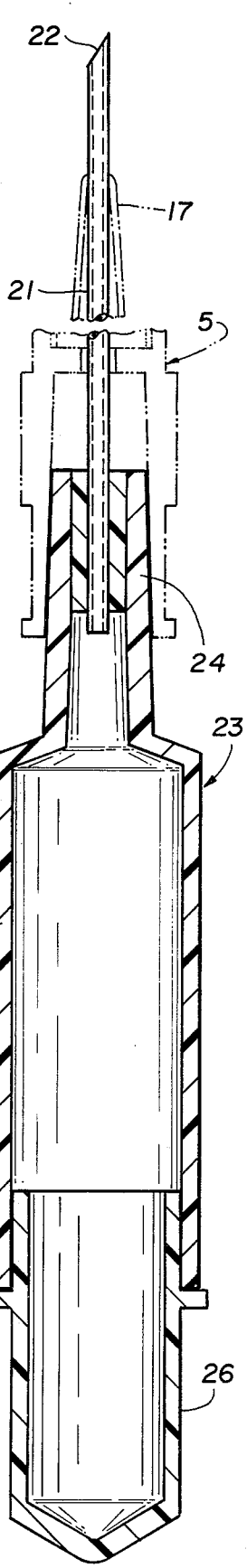
FIG. 4 is a longitudinal section, partly in elevation, of the puncture needle for initial use with the I.V. tube, the distal end of the tube and the proximal end of the connecting hub being indicated in dotted lines.

For this purpose, and as shown in FIG. 4 of the drawings, the invention also provides a hollow, relatively rigid, puncture needle 21 having a length such that when carried within the flexible I.V. tube, its pointed distal end 22 extends distally beyond the hollow tip 17 and its proximal end is firmly affixed to a hollow manipulating handle generally indicated 23.

The handle 23 preferably is formed from an inert transparent moldable plastic such as polyethylene or polypropylene or other suitable material and includes a generally cylindrical distal end 24 into which the proximal end of the needle 21 is embedded and having a length and diameter to be closely received by and frictionally retained within the hub cavity 6. The handle also includes a relatively long, cylindrical, grasping and manipulating portion 25, the proximal end of which is adapted to receive and frictionally retain a removable closure plug 26. The cylindrical portion 25, being transparent, also serves as a sight zone in the handle.

The complete unit is assembled as indicated in FIG. 4 of the drawings so that it is relatively rigid at the time its distal end is introduced into a vein through the initial penetration effected by the puncture needle 21 and the distal tip 17. At this point, if a blood sample is to be taken, the unit is further advanced into the vein a distance sufficient for the sample to be extracted and the proximal plug 26 is removed to permit connection to the barrel of a syringe. After the blood sample is taken the needle is removed from the I.V. tube, thus making the cavity 6 of the hub 5 available for connection to a source of I.V. fluid and permitting the further flexible introduction of the I.V. tube to the desired length of advance within the vein.

It will have been understood from the foregoing description that the only time that the assembly is in a relatively rigid state is when the puncture needle 21 is in place as an incident to the initial insertion within a vein and that thereafter, when the needle has been removed, the I.V. tube can flex during its further advance into the vein and can thereafter continue to flex in accordance with the demands imposed by the patient's movements so long as it remains inserted. Further, since the entire construction is of materials that are inert and since the hub 5 is adapted to be coupled and recoupled to the source of I.V. fluid, there is no need to remove the I.V. tube after each I.V. feeding, as has been required in the past with other types of I.V. feeding devices.

It also should be mentioned that while the hub 5 and sleeve 12 have been described as preferably formed from metal, suitable plastic materials also can be used with equal effect, with suitable variations in the assembly technique.

Further, although the outer sheath 15 preferably is formed from heat-shrinkable plastic tubing as described, other techniques may be employed to form the outer sheath.

For example, the spring 13 can be coated by being dipped in a solvent solution, dispersion or emulsion of the desired plastic, then removed and dried. In this technique a wire mandrel, to which the plastic is non-adhering, is inserted through the lumen of the spring with one end projecting distally therebeyond to permit the hollow tip 17 to form therearound, the proximal end of the wire mandrel would be provided with a cylindrical cap that fits over the proximal end of the spring in order to provide clearance between the proximal end of the spring and the formed coated outer sheath to permit proper fitting over the distal end of the sleeve 12.

In the event that it is desired to use a dispersion of a fluorinated hydrocarbon, such as a commerically available "Teflon" 120 or "Teflon" 30 B, to form the outer sheath, the method of application advantageously could be as disclosed and claimed in U.S. Pat. No. 3,922,378, granted Nov. 25, 1975.

Figure 5:
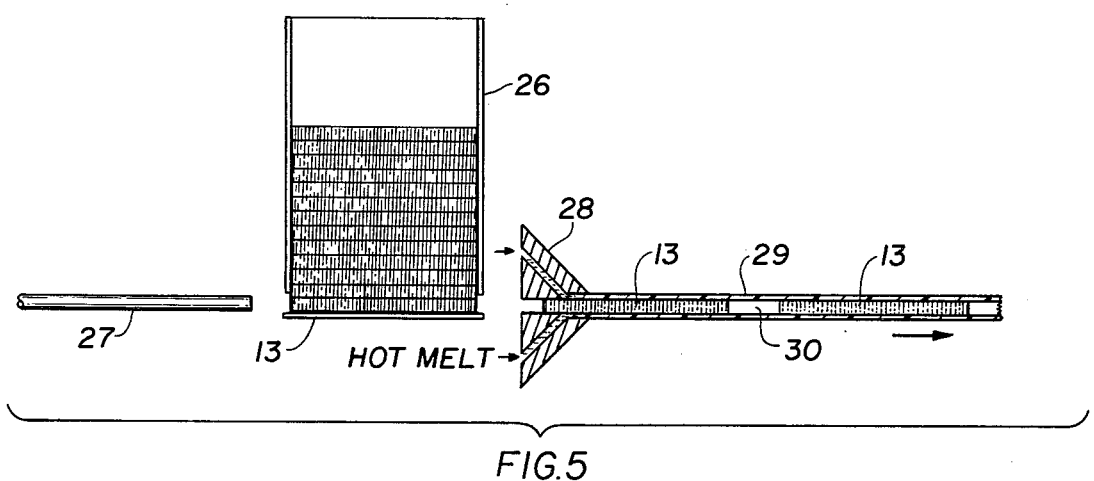
FIG. 5 is a schematic diagram of a method of applying the outer sheath to the body spring by extrusion coating.
Figure 6:
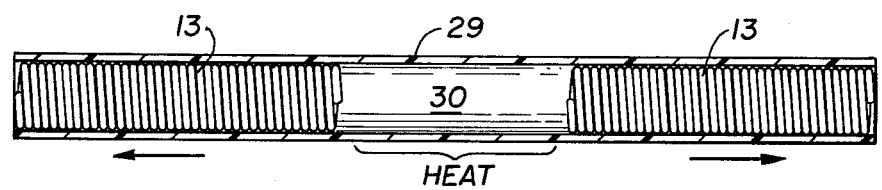
FIG. 6 is an enlarged longitudinal section of an opposed twin unit severed from the continuous production of FIG. 5.
Figure 7:
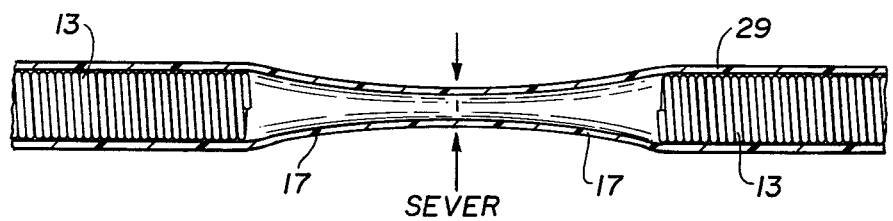
FIG. 7 is a detail of the mid portion of the twin unit of FIG. 6 and shows the configuration of the extruded tubing between the body springs after heat and tension draw down has been effected.

However, when large quantities of these flexible I.V. tubes are to be manufactured, such manufacture may be expedited by extrusion coating the outer sheath onto the spring as schematically indicated in FIGS. 5–7 of the drawings.

Basically, in such an extrusion coating system a supply of the body springs 13 are stacked in a magazine 26 and are individually removed therefrom in an axial direction by a reciprocating ram 27 which feeds each spring into the center of an extrusion die 28 from which a continuous tube 29 of the desired hot melt plastic is extruded and becomes firmly bonded to the outer surface of each spring. Separation between the springs is effected by the timing and stroke length of the ram 27 to leave a gap 30 having a length at least twice that of the finished length of the hollow distal tip 17 of the I.V. tube.

Each successive pair of spaced extrusion coated springs is severed from the continuous production thereof to form an opposed twin unit as indicated in FIG. 6. At this stage heat is applied to the extruded tubing around the middle portion of the gap 30 and simultaneously the two extrusion coated springs are pulled in opposite directions, as indicated by the arrows, to stretch the heated tubing and effect a draw down to the desired taper and diameter of what becomes a pair of joined opposed distal tips 17, 17, as indicated in FIG. 7, which are then severed at the mid-point to provide two coated body tubes each having a properly tapered distal tip. As before, the raw edges of the distal tips 17 are smoothed either by the application of heat or by grinding and polishing.

The above described method of extrusion coating provides spring units having proximal ends that are adapted to be received in and retained by plain socket types of hub fittings, i.e. those that do not include the sleeve 12.

Figure 8:
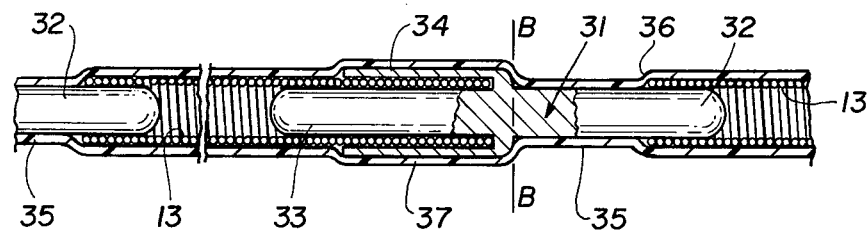
FIG. 8 is an enlarged longitudinal section showing a modification of the extrusion method by which the extrusion is given a bell configuration at the proximal end of each spring.

However, the same general method of extrusion coating readily may be modified, as schematically indicated in FIG. 8, to provide a bell configuration to the extrusion at the proximal end of each spring, which configuration fits over the upper end of the sleeve 12 in the annular void between it and the wall of the cavity 11.

In this extrusion modification the springs 13 are serially connected by non-adherent or release-coated insert pins generally indicated 31, each of which includes an end 32 that frictionally fits within the distal end of one spring and an end 33 that frictionally fits within the proximal end of the adjacent spring. An annular skirt 34 surrounds the pin end 33 and is spaced therefrom a distance sufficient to receive the proximal end of its associated spring and has a length equal to the depth of that part of the extruded coating or sheathing that is to be fitted over the upper end portion of the hub sleeve 12.

The thus pin-connected springs are continuously fed through the extrusion die as before and are wound on a large diameter reel for storage and transfer to finishing operations. The extrusion coated springs are finished for connection to the hub 5 simply by cutting through the extruded sheathing in the plane B—B of FIG. 8, pulling the right hand spring 13 off its associated pin end 32 and then pulling the insert pin 31 out of the left hand spring 13. This leaves the right spring 13 with a hollow distal tip 35 that is necked down at 36 to restrain the distal end coils of the spring against axial elongation. The tip 35 can then be tapered as desired by heat-drawing or other suitable techniques and the raw edge at the exposed end can be smoothed as described before. This also leaves the left spring 13 with a proximal end annular bell 37 defined by the sheathing and separated from the adjacent portion of the spring a distance sufficient to fit over the upper end of the hub sleeve 12 as mentioned above.

It is of course to be understood that variations in arrangements and proportions of parts may be made within the scope of the appended claims.

I claim:

1. A flexible intra-venous feeding tube including an inner body having proximal and distal ends and formed from stainless wire as a continuously wound lumen-defining helical spring with a majority of the helices thereof in contact with each other; an uninterrupted externally smooth transparent outer sheath having proximal and distal ends and formed from an inert plastic material so applied around said spring that its inner surface is firmly bonded thereto except at the proximal end portion thereof, the proximal end portion of said outer sheath being radially spaced from the adjacent of said spring whereby to define an annular void therebetween, the distal end of said outer sheath extending beyond the distal end of said spring and shaped to define a distally tapered hollow tip having an open distal end, a plurality of the helices of said spring being separated intermediate the proximal and distal ends thereof to provide a sight zone for visual observation of liquid flow; and a connected hub sealingly secured to the proximal ends of said spring and its said outer sheath, said hub having a proximal end portion provided with an axial socket for the initial retention of the handle of a puncture needle and for subsequent connection to a source of feeding liquid and terminating inwardly in a transverse web provided with a central aperture, said hub having a distal end bell housing provided with two serially arranged cylindrical cavities coaxial with said central aperture, the distal one of said cavities having a diameter greater than that of the other thereof, a rigid sleeve affixed within the smaller diameter of said cavities and having a length to extend distally beyond the distal end of said bell housing, said sleeve having an inside diameter to receive and retain the unsheathed proximal end portion of said spring, means for securing the said proximal end portion of said spring within said sleeve, the proximal end of said outer sheath being fitted over the distal end portion of said sleeve and extending proximally into the annular void defined by the outer surface of said sleeve and the inner surface of said larger diameter cylindrical cavity, at least a portion of the wall of said larger diameter cavity being radially displaced inwardly whereby to secure the said proximal end portion of said outer sheath against the adjacent portion of said sleeve within said larger diameter cavity.

2. The intra-venous feeding tube of claim 1 additionally including a plastic reinforcing sleeve surrounding the proximal end portion of said outer sheath and extending distally beyond the distal end of said bell housing.

3. The intra-venous feeding tube of claim 1 in which said spring and said hollow tip are internally coated.

4. The intra-venous feeding tube of claim 3 in which said internal coating is formed from the same type of plastic as that of said outer sheath.

5. The intra-venous feeding tube of claim 1 additionally including a puncture needle comprising a hollow needle extending through the lumen of said tube and having a sharpened distal end extending distally beyond the distal end of said hollow tip, a distal end portion of said needle being frictionally retained within the distal end portion of said hollow tip, said needle having a proximal end extending proximally through the same central aperture of said connector hub, and a manipulating handle affixed to the proximal end of said needle, said handle being hollow and formed from a transparent plastic material, said handle including a distal end complementary to the said proximal socket of said connector hub for frictional retention therein, a proximally extending body portion, and a removable plug closing the proximal end of said body portion, the distal end and the body portion of said handle being in open communication with the lumen of said needle.

* * * * *